United States Patent [19]

Freepons

[11] Patent Number: 4,999,048

[45] Date of Patent: Mar. 12, 1991

[54] METHOD FOR REDUCING PESTICIDE DRIFT

[75] Inventor: Donald Freepons, Kennewick, Wash.

[73] Assignee: Canbra Foods Ltd., Alberta, Canada

[21] Appl. No.: 410,423

[22] Filed: Sep. 21, 1989

[51] Int. Cl.$^5$ .................... A01N 37/18; A01N 37/38; C07D 303/38

[52] U.S. Cl. .................. 71/118; 71/DIG. 1; 71/117; 71/88; 549/549; 549/557

[58] Field of Search ..................... 71/DIG. 1, 88, 117, 71/118; 549/549, 557

[56] References Cited

PUBLICATIONS

L. F. Bouse et al., "Effect of Spray Mixture on Droplet Size" An ASAE/CSAE Meeting Presentation, Jun. 25–28, 1989, Paper No. 891006.

J. B. Carlton, "Aerial Spray Deposit Analysis II: A Spray Displacement Index"; An ASAE Meeting Presentation; Jun. 24–27, 1990, Paper No. 901020.

L. F. Bouse et al., "Atomization of Vegetable Oils in an Airstream" Transactions of the ASAE (vol. 32, No. 6, pp. 1829–1836, 1989).

Primary Examiner—Richard L. Raymond
Assistant Examiner—Brian Bembenick
Attorney, Agent, or Firm—Lorusso & Loud

[57] ABSTRACT

A method for reducing pesticide drift caused by crystallization of a pesticide from a pesticide spraying formulation. Crystallization of a pesticide from a pesticide spraying formulation is suppressed by incorporating an expoxidized vegetable oil into the formulation. The method increases pesticidal efficacy of a pesticide applied in the form of a pesticide spraying formulation. A pesticide spraying formulation is provided which comprises a pesticide, a diluent and an epoxidized vegetable oil.

25 Claims, 3 Drawing Sheets

FIG. 1
PROPANIL 1 PART
WATER 6 PARTS
F-7 0 SEC.

FIG. 2
PROPANIL 1 PART
WATER 6 PARTS
F-7 24 SEC.

FIG. 3
PROPANIL 1 PART
WATER 6 PARTS
F-7 3 MIN. 15 SEC.

FIG. 4

PROPANIL   1 PART
CANOLA EO 1 PART
WATER     5 PARTS
0 MIN.

FIG. 5

PROPANIL   1 PART
CANOLA EO 1 PART
WATER     5 PARTS
1 MIN. 20 SEC.

FIG. 6

PROPANIL — 1 PART
CANOLA EO 1 PART
WATER 5 PARTS

FIG. 7

PROPANIL — 1 PART
WATER — 6 PARTS

METHOD FOR REDUCING PESTICIDE DRIFT

BACKGROUND OF THE INVENTION

This application relates to a method for controlling and reducing pesticide drift. More particularly, the application relates to a method for controlling and reducing pesticide drift caused by crystallization of pesticides from liquid spraying formulations.

Pesticides, which are chemicals poisonous to selected organisms, are used mainly in agriculture and forestry to control insects (insecticides), weeds (herbicides), fungi (fungicides) and other pests. Although the use of pesticides is viewed as beneficial, mainly because of increased agricultural yields, it is also responsible for many undesirable effects, including crop damage to nearby plants susceptible to the toxins, environmental pollution and human illnesses. Even when properly used, chemical pesticides have a number of unavoidable side effects. These problems due to inherent toxicity of pesticides are frequently amplified by the phenomenon of pesticide drift, i.e. the transport or movement of the toxic chemicals away from the intended area of deposition.

Pesticide drift is principally caused by airborne movement of particles or droplets produced when pesticides in the form of liquid formulations are sprayed over an area of application to ensure an even coverage of the area. Such an operation normally produces a wide range of droplet sizes including very small droplets which are buoyed up by air and may travel in the wind direction over substantial distances, causing an uncontrolled spread of pesticides.

In the United States approximately 300,000,000 acres receive pesticide application each year. Aerial applications, mainly by fixed wing aircrafts, are made to over 60% of this area (Ferguson, W. L., "Farmers Expenditures for Custom Pesticide Services", 1971 USDA AER #314, Nov. 1975). The extent of the problem caused by pesticide drift may be illustrated by damage claims reported by the insurance industry. For example, between June 1979 and July 1980, claims for crop damages caused by spray drift totalled U.S. $130,000,000, i.e. about 43 cents for every acre that was sprayed. Statistics of this kind do not even include environmental damage caused by the uncontrolled spread of pesticides.

As mentioned above, about ⅗ of the acreage receiving a pesticide application in the United States are aerially sprayed. When spraying formulations are applied to a field by an airplane, great quantities of small droplets are formed from normal atomization by spraying nozzles and by wind shear as the nozzles release the sprayed liquid through the air at 80 to 120 mph. These small droplets, typically less than 100 microns in diameter, may travel over large distances buoyed up by the air, thus causing a substantially uncontrollable spread of pesticides. Also as these small droplets fall toward the ground, the evaporation of the solvent or diluent, usually water, further reduces the size of the droplets. With evaporation the droplets shrink to particles composed mainly of the active ingredient and a small portion of the diluent and having frequently a size in the range of a few microns, i.e. forming an aerosol with practically unlimited drift ability. This small particle drift mechanism, due to evaporation of the diluent from the spray formulation, is common to all pesticides applied in the form of solutions and suspensions. Spray drift may also affect larger droplets. Since the extent of evaporation is mainly determined by the time during which droplets fall to the ground, droplets that are originally even substantially larger than 100 microns but that are caught up in the wing-tip vortices and flung 40 to 60 feet in the air have enough time to lose by evaporation most of the diluent while falling to the ground and to be reduced to small particles easily transportable over large distances by natural air movements. It is estimated that, due to drift, up to about 50% of the sprayed material never reaches the ground in the intended area of application when applied by an aircraft flying at a height of 7.5 feet above the ground and that this loss increases to about 80% if the application height is 30 feet (Avant, R. V. et al, "Pesticide Deposition vs Drift: The Alternatives", ASAE 79-3556, 1979; Potts, F. S., Journ. Econ. Ent. 39: 716–712, 1946).

Pesticide drift may be also caused by the volatilization of the pesticide, as exemplified by esters of 2,4,-dichlorophenoxyacetic acid (2,4-D), in which case the pesticide itself may substantially vaporize from the applied material and drift in the gaseous form. This type of drift is frequently referred to as vapour drift.

Different factors, such as meteorological conditions, spray equipment, type of aircraft, chemical characteristics of pesticide, operator skill, etc. may influence all types of drift. Typically, the risk of drift is increased in aerial spraying and when high pressure, small nozzle tips are used in the spraying equipment. Also the spread of pesticides applied in the form of mists and dusts is usually more difficult to control.

When the pesticide is a solid material applied as a dust formulation, such as early DDT applications, there is a danger of the dust being moved even by a slight breeze over the target, either while being applied or after the application is made.

Some solid pesticides pose particular drift problems due to their strong tendency to crystallize from liquid formulations in which they are applied. When a liquid formulation comprising such a pesticide is sprayed and the diluent or solvent evaporates from the spray droplets, a large number of small crystals is rapidly formed. These crystals have their size and weight substantially reduced with respect to those of the original droplets and are easily moved by wind over large distances. Part of the material is deposited on the target site in droplets big enough to reach it before crystallization takes place. After evaporation of solvent also these droplets can release the active ingredient in the form of small crystals which may be moved by winds as if they were a dust formulation.

An example of such a pesticide is propanil (3′,4′-dichloropropionanilide) which is a contact herbicide of particular value for post-emergent control of grass weeds in rice, especially of barnyard grass. Barnyard grass is one of the most troublesome weeds of this crop. Propanil is a very effective and inexpensive herbicide for use with rice crops, but its strong tendency to crystallization and spray drift problems related to it, have resulted in very strict application controls.

Propanil is a water-insoluble substance supplied to the user in the form of an emulsifiable concentrate, typically as 50% by weight solution in a mixture of ketones. For spraying purposes this concentrate is diluted with water in a spray tank prior to spraying. It is believed that this dilution may cause partial crystallization of propanil in the spray tank, thus speeding up the process of crystallization after spraying, further accelerated by evaporation of water from the droplets.

To keep the water diluent from evaporating too quickly, various additives are typically incorporated into pesticide spraying formulations. The literature indicates that petroleum oils have been used as spray additives for certain pesticides and crops but were found to be quite often phytotoxic. The use of other additives, such as surfactants, sticker/spreaders, water viscosity modifiers (polyvinyl alcohol, alginates, starches etc.) is also known. While these additives may produce measurable differences in evaporation rates and viscosities of spraying compositions, they do not significantly suppress or reduce pesticide drift.

Vegetable oils, such as cottonseed oil are sometimes used as spraying additives. According to Akessen, Yates, Brazelton and Natwick (paper No. 83-1510, "Laboratory and Field Studies on Vegetable Oil-Based Spray Applications", American Society of Agricultural Engineers, Chicago, Dec. 13-16, 1983) when cottonseed oil was used in combination with propanil concentrate, as the ketone evaporated, crystals of propanil appeared as "striations" on the oil surface. The formation of crystals of propanil was also observed from a formulation comprising 20% of cottonseed oil, 10% of herbicide and 70% of water (by volume). As can be seen from the above, vegetable oils are not efficient in preventing the crystallization of propanil and, consequently, spray drift.

SUMMARY OF THE INVENTION

It has been now found that pesticide drift due to crystallization of pesticides from spraying formulations may be eliminated or substantially reduced by incorporating epoxidized vegetable oils as crystal-inhibiting components into spraying formulations.

It is accordingly an object of the invention the invention to provide a method for reducing pesticide drift caused by crystallization of a pesticide from a pesticide spraying formulation, which method comprises incorporating an epoxidized vegetable oil into the formulation.

It is another object of the invention to provide a method for suppressing crystallization of a pesticide from a pesticide spraying formulation, which method comprises incorporating an epoxidized vegetable oil into the formulation.

According to still another object, the invention provides a method for increasing the pesticidal efficacy of a pesticide applied in the form of a spraying formulation, which method comprises incorporating an expoxidized vegetable oil into the formulation.

The method of this invention is a process that inhibits, suppresses or delays pesticide, particularly propanil, crystallization to a degree that it is undetectable in the airflow off of the sprayed field. Surprisingly and unexpectedly, it was found that propanil crystals do not form or are greatly delayed in forming when epoxidized vegetable oil, particularly soy or canola oils, are mixed with a pesticide, particularly propanil, in a liquid, particularly aqueous solution, which solution is aerially applied to crops, particularly rice fields for weed, particularly watergrass or barnyard control.

The invention discloses the use of epoxidized vegetable oils to intervene and function as a co-agent with a pesticidally active ingredient, such as propanil, and not as a modifier, adjustor or manipulator of the liquid phase of the sprayed solution. Although the functioning of epoxidized vegetable oils is not fully understood at this time, these products possess a capacity to misce or dissolve the propanil formulation or attach to the propanil molecule in such a way as to maintain the propanil in solution.

This retention significantly reduces the "up-lift" loss of the active ingredient from the field by air movements thus increasing the quantity of active ingredient which remains "onsite" after deposit. Due to this fact the application rate can be reduced or fewer applications are needed to effect pest control, which reduces the economic expense. Also the environmental impact due to pesticide contamination off target site is substantially reduced. Since the additives according to the invention are safe, biodegradable materials, they do not contribute to environmental pollution.

DESCRIPTION OF THE PREFERRED EMBODIMENTS

This invention discloses the unique capacity of epoxidized vegetable oils to interact with pesticides, such as propanil, in pesticide formulations to inhibit, suppress or delay crystallization of active ingredient during and after a foliar application.

The term "vegetable oils" refers to, generally, oils derived from plant sources. More particularly, it is intended to include "fixed" oils of both drying and nondrying types, containing substantial amounts of unsaturated fatty acids, such as oleic acid, linoleic acid, linolenic acid, eicosenoic acid and erucic acid. These acids are frequently characterized by two numbers separated by a colon, e.g. 18:1, wherein the first number identifies the number of carbon atoms in the molecule of fatty acid while the second number refers to the number of carbon-carbon double bonds. Examples of suitable oils are soybean oil, rapeseed oil (both high erucic and low erucic, called canola oil), cottonseed oil, sunflower oil, safflower oil, tall oil, palm kernel oil, coconut oil, jojoba oil, corn oil, peanut oil, olive oil and linseed oil. Fatty acid compositions of some of these oils are provided in Table 1. The vegetable oils are available as refined, unrefined or extracted oils. Canola oil and soybean oil are preferred.

The epoxidized vegetable oils may be prepared from respective unepoxidized oils using methods known per se. Some epoxidized vegetable oils are produced for other purposes, such as high purity epoxidized soybean oil approved for use in food packaging materials.

The epoxidized oils may be mixed with a pesticide in a ratio of from about 1:10 to about 10:1 (v/v, epoxidized vegetable oil to pesticide liquid concentrate). The ratio of 1:1 is preferred. A mixture of epoxidized oil and pesticide may be diluted with a suitable diluent, preferably water, to provide a spraying formulation. Alternatively, a pesticide concentrate may be diluted with a diluent and an epoxidized oil added to this mixture in suitable proportion to prepare a spraying formulation.

Further additives, such as binders, dispersants and emulsifiers may be incorporated into the formulations. Ammonium lignin sulfonate (ALS) is a preferred additive. ALS is one of a family of ligno-sulfonates produced as a by-products in the pulping of wood. It has been found that spraying formulations containing ALS show improved crystal suppression and spray retention onto the target. ALS is normally used as 50% by weight aqueous solution and may be mixed in this form with a pesticide concentrate in a ratio of from about 1:10 to about 10:1 (v/v, ALS solution to pesticide concentrate). The ratio of 1:1 is preferred.

TABLE 1

Some Important Fatty Acids of Refined Vegetable Oils in Canada (W/W %)

| Fatty Acid | Rapeseed[a] (High erucic) | Canola[b] (var Regent) | Soybean[b] | Corn[b] | Peanut[a] | Sunflower | Olive[a] | Palm[a] |
|---|---|---|---|---|---|---|---|---|
| 16:0 | 4 | 4 | 9 | 11 | 13 | 6 | 14 | 46 |
| 18:0 | 2 | 2 | 5 | 2 | 3 | 4 | 2 | 8 |
| 18:1 | 34 | 55 | 45 | 27 | 42 | 19 | 64 | 3 |
| 18:2 | 17 | 26 | 37 | 59 | 34 | 69 | 16 | 10 |
| 18:3 | 7 | 10 | 3 | 1 | tr | tr | — | tr |
| 20:1 | 9 | 2 | tr | tr | tr | — | — | — | tr-Trace
[a]Adapted from Ackman (1977)
[b]Stevenson et al. (1981)

EXPERIMENTAL

Various tests were devised for studying the influence of epoxidized vegetable oils on the behaviour of propanil formulations under various conditions. Commercially available concentrate of propanil (STAM 4M ™ of Rohm and Haas) was used in most of these tests, unless otherwise stated.

The expoxidized vegetable oils were prepared by Viking Chemical Company and had the typical characteristics shown in Table 2.

TABLE 2

| Representative epoxidized vegetable oils | | | | |
|---|---|---|---|---|
| | refined canola oil | degummed canola oil | non-degummed canola oil | soy oil |
| oxirane oxygen, % | 6.47 | 5.74 | 5.70 | 7.0–7.2 |
| iodine value | 2.60 | 1.14 | 1.16 | 2.0 |
| acid value | 0.26 | — | 0.15 | 0.3 |
| viscosity, stokes | 2.7 | — | — | 3.2–4.2 |

Ammonium lignin sulfonate (ORZAN A, trade mark of ITT Rayonier Inc.) had the following typical characteristics:

| | |
|---|---|
| Sodium | 6.0% |
| Calcium | 0% |
| Ammonia (N) | 2.5% |
| Methoxyl | 7.6% |
| Sulfur (as S) | 6.2% |
| Sulfite (as S) | 0.1% |
| Sulfate (as S) | 0.5% |
| Ash | 2.5% |
| Reducing Substances | 28.0% |
| Free Sugars | 21.0% |
| Lignosulfonate | 65.0% |
| pH | 4.0 |

This material was used in tests as 50% by weight aqueous solution (designated as AL-50).

EXAMPLE 1

Evaluation Of Crystal-Inhibiting Properties— evaporation dish test

Figure 6:
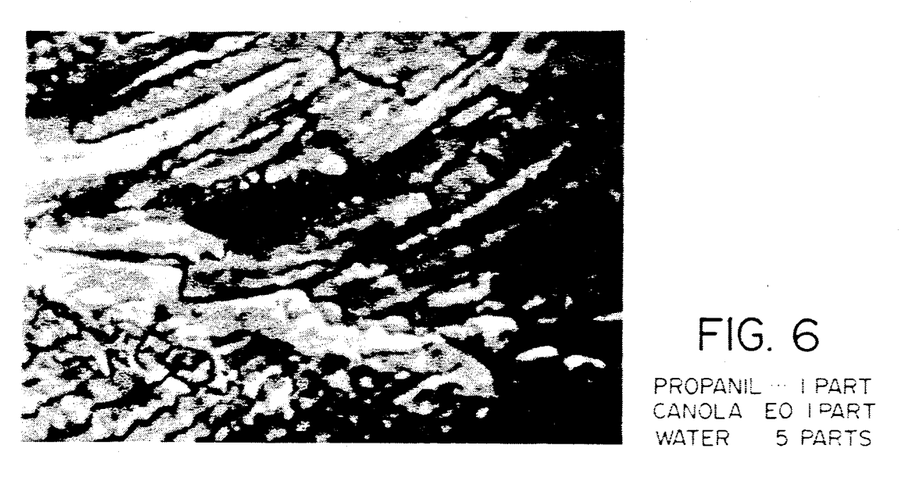
FIG. 6 is a macrophotograph of a residue of propanil/water spraying formulation after evaporation of volatile components.
Figure 7:
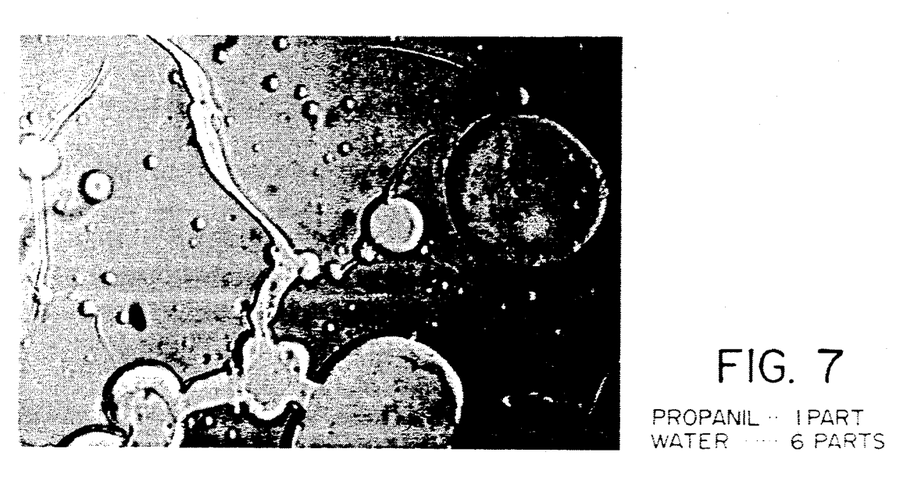
FIG. 7 is a macrophotograph of a residue of propanil/water/expoxized canola oil spraying formulation after evaporation of volatile components.

A preliminary evaluation of crystal-inhibiting properties of various additives was conducted by an evaporation dish test. For this test 2 ml (0.96 g) of propanil concentrate were mixed with 0.48 g of an additive (epoxidized canola oil or epoxidized soybean oil and optionally Epox 828) until completely dissolved. The solution was then distributed in the form of a thin layer into an aluminium evaporation dish and left at ambient temperature for the evaporation of volatile components of the formulation. After a period of up to 400 hours, the dish was visually inspected for the presence of propanil crystals. The results of this test are summarized in Table 3 and illustrated by FIGS. 6 and 7. FIG. 6 shows large, easily fractured crystals developed during evaporation of voltatile components from a water based propanil formulation (formulation No. 7, Table 4). No identifiable crystals can be seen in FIG. 7 which shows the results of evaporation under similar conditions of a formulation containing epoxidized canola oil (formulation No. 3, Table 4).

TABLE 3

| EPOXIDIZED SOY OIL | | | | |
|---|---|---|---|---|
| Sample # | Propanil | Epoxidized Soy Oil | Propanil/oil ratio | Results |
| 1 | .96 g | 0.48 g + 0.48 g Epox 828* | 2:1:1 | no crystals after 24 hr; a few small crystals after 48 hr |
| 2 | .96 g | 0.96 g | 1:1 | no crystals after 24 hr; a few crystals forming after 48 hr |
| 3 | .96 g | 0 | 1:0 | crystallizing after 24 hr; crystallized (dry) after 48 hr |

| EPOXIDIZED CANOLA OIL | | | | |
|---|---|---|---|---|
| Sample # | Propanil | Epoxidized Canola Oil | Propanil/oil ratio | Results |
| 1 | 1.92 g | 0 | 1:0 | Crystallized |

Figure 4:
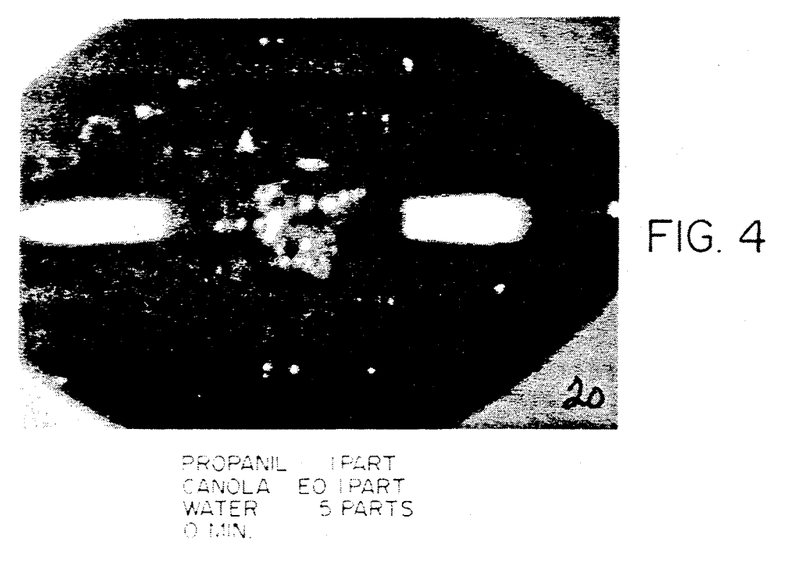
FIG. 4 is a macrophotograph of a droplet of propanil/water/epoxidized canola oil spraying formulation deposited on a wire.
Figure 5:
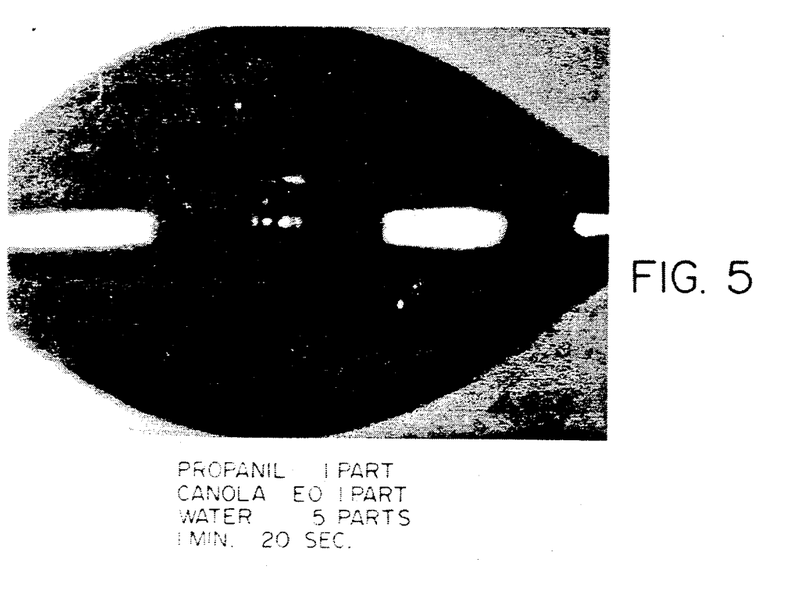
FIG. 5 is a macrophotograph of the droplet of FIG. 4 1 minute 20 seconds after deposition.

TABLE 3-continued

| | | | | |
|---|---|---|---|---|
| | | | | completely after 27 hr |
| 2 | 1.92 g | 0.48 g | 4:1 | Crystallized at edges after 27 hr |
| 3 | 1.92 g | 0.96 g | 2:1 | A few crystals at edges after 27 hr |
| 4 | 1.92 g | 1.92 g | 1:1 | A few crystals forming after 48 hr; Some crystals forming after 120 hr |
| 5 | 1.92 g | 3 84 g | 1:2 | No crystals forming after 400 hr |

*Diglycidal ether of bisphenol-A of Shell Chemical Co.

EXAMPLE 2

Evaluation Of Crystal-Inhibit Properties—wire test

The influence of epoxidized canola oil on evaporation rate of water based propanil formulations was evaluated by catching on a 60 micron wire droplets of ca. 200 microns in diameter intended to simulate effects of an aerial spraying. The droplets deposited on the wire were observed under microscope to determine the rate of evaporation. The results of this experiment are summarized in Table 4. FIGS. 1, 2 and 3 show the results of the experiment for a water based propanil formulation (formulation No. 7, Table 4). A substantial loss of water from a droplet after only 24 seconds can be seen from FIG. 2, whereas FIG. 3 shows total loss of water after 3 min. 15 sec. Only a minimal loss of water from a droplet of a similar propanil formulation containing epoxidized canola oil (formulation No. 3, Table 4) after 1 min. 20 sec. under similar conditions may be observed on FIGS. 4 and 5.

TABLE 4

| Formulation # | Propanil | Composition [parts] ECO | ALS | Water | Surface Tension [dynes/cm] | Viscosity [centipoise] | Shear rate [$sec^{-1}$] | Density [$g/cm^3$] | Time | Diminishment |
|---|---|---|---|---|---|---|---|---|---|---|
| 1 | 1 | 1 | 0 | 0 | 38.8 | 83.22 | 150 | 1.035 | 7 min | neg. |
| 2 | 1 | 2 | 0 | 0 | 41.7 | 307.71 | 75 | 1.059 | 7 min | neg. |
| 3 | 1 | 1 | 0 | 5 | 38.0 | 2.00 | 1500 | 1.012 | 7 min | 10% |
| 4 | 1 | 2 | 0 | 4 | 37.7 | 5.89 | 1500 | 1.012 | 7 min | 10% |
| 5 | 1 | 1 | 1 | 4 | 37.7 | 4.35 | 1500 | 1.044 | 3 min 45 sec | 10% |
| 6 | 1 | 2 | 1 | 3 | 41.0 | 9.42 | 1500 | 1.043 | 3 min 45 sec | 10% |
| 7 | 1 | 0 | 0 | 6 | 41.0 | 2.79 | 1500 | 1.046 | 45 sec | 30% |
| | | | | | | | | | 3 min 45 sec | 100% |

ECO - epoxidized canola oil
ALS - ammonium lignin sulfonate
All physical characteristics measured at 25° C.

EXAMPLE 3

Efficacy Tests

Efficacy greenhouse trials to evaluate possible differences in the herbicidal potency of propanil formulations both containing epoxidized canola oil and without an oil additive, and to identify efficacy levels of the herbicide in the various tank mixes as would be applied to a field have also been conducted.

For the tests, 6 rice seeds and 6 watergrass seeds were planted in separate pots with 5 replications of each group. The plants were sprayed with herbicidal formulations shown in Table 5 after reaching the following approximate stages of development:

rice plants: 4 leaf stage, height about 10 cm, weight about 2g;

barnyard grass: 5 leaf stage, height 18 to 23cm, weight about 8g, starting to tiller.

Figure 1:
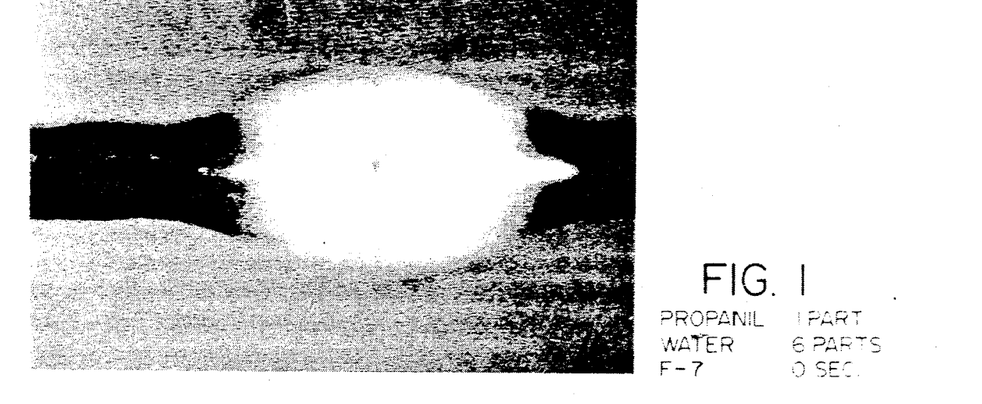
FIG. 1 is a macrophotograph of a droplet of propanil/water spraying formulation deposited on a wire.
Figure 2:
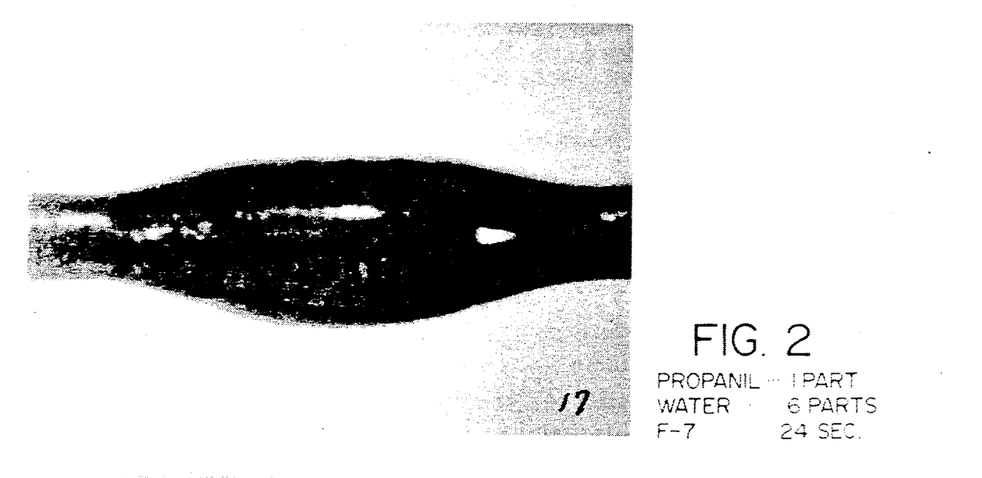
FIG. 2 is a macrophotograph of the droplet of FIG. 1 24 seconds after deposition.
Figure 3:
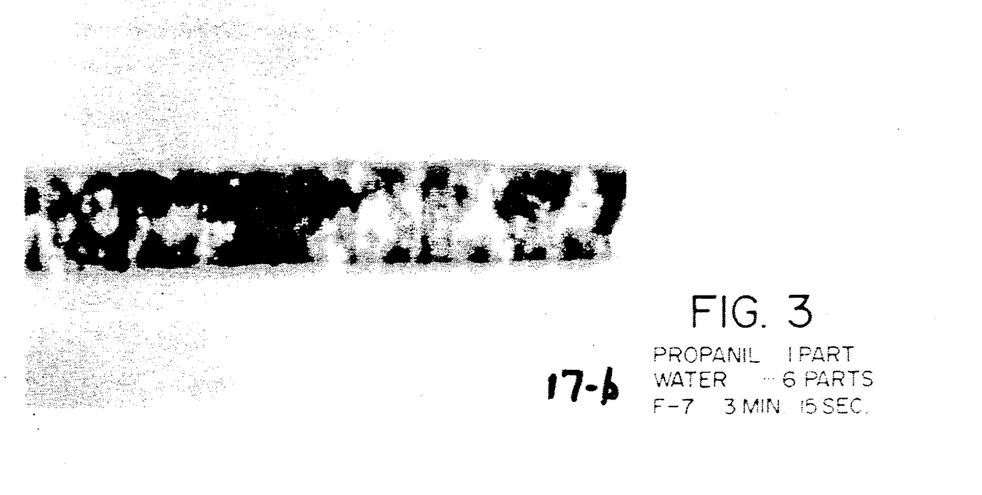
FIG. 3 is a macrophotograph of the droplet of FIG. 1 3 minutes 15 seconds after deposition.

The spraying formulations include two control formulations prepared without the oil additive (treatment Nos. 7 and 9) and pure water (treatment No. 10). 5 days after spraying the barnyard grass plants were collected and measured. The calculated averages are summarized in Table 5.

These data show that the addition of epoxidized canola oil and ammonium lignin sulfonate to a propanil/water spray solution does not decrease the herbicidal efficacy of propanil on barnyard grass, but that the herbicidal activity of these formulations is equal to that of propanil/water treatment. With the exception of treatment No. 6 the results of all treatments comprising epoxidized canola oil are within 1% of the value of the propanil/water treatment. Interestingly, the increase of propanil application rate by 25% (treatment No. 9) did not demonstrate an appreciable improvement in the herbicidal efficacy.

TABLE 5

PROPANIL EFFECTIVENESS ON BARNYARD GRASS

| Treatment No. | Propanil* | ECO* | AL-50* | Water* | Typical application rate Gal/Acre | Average Pot Population | Survival % of Six | Average Plant Height, cm | Average Plant Weight per pot, g. | Average weight/plant | Average weight/plant as % of control (treatment) No. 10) |
|---|---|---|---|---|---|---|---|---|---|---|---|
| 1 | 1 | 1 | 0 | 0 | 2 | 4.4 | .7333 | 66.1 | 30.03 | 6.8 g | 38 |
| 2 | 1 | 2 | 0 | 0 | 3 | 5.6 | .9333 | 75.4 | 39.95 | 7.1 g | 39 |
| 3 | 1 | 1 | 0 | 5 | 7 | 4.8 | .8000 | 70.2 | 31.01 | 6.5 | 36 |
| 4 | 1 | 2 | 0 | 4 | 7 | 4.6 | .7666 | 72.4 | 24.79 | 5.4 | 30 |
| 5 | 1 | 1 | 1 | 4 | 7 | 4.0 | .6666 | 76.4 | 28.22 | 7.1 | 39 |

TABLE 5-continued
PROPANIL EFFECTIVENESS ON BARNYARD GRASS

| Treatment No. | Propanil* | ECO* | AL-50* | Water* | Typical application rate Gal/Acre | Average Pot Population | Survival % of Six | Average Plant Height, cm | Average Plant Weight per pot, g. | Average weight/plant | Average weight/plant as % of control (treatment) No. 10) |
|---|---|---|---|---|---|---|---|---|---|---|---|
| 6 | 1 | 2 | 1 | 3 | 7 | 4.4 | .7333 | 79.0 | 42.41 | 9.6 | 53 |
| 7 | 1 | 0 | 0 | 6 | 7 | 3.8 | .6333 | 77.8 | 25.87 | 6.8 | 38 |
| 8 | 0 | 1 | 1 | 5 | 7 | 5.6 | .9333 | 91.0 | 98.23 | 17.5 | 97 |
| 9 | 1.25 | 0 | 0 | 5.75 | 7 | 4.6 | .7666 | 81.2 | 30.85 | 6.7 | 37 |
| 10 | 0 | 0 | 0 | 7 | 7 | 5.8 | .9666 | 85.0 | 105.1 | 18.11 | 100 |

ECO - opoxidized canola oil
AL-50 - ammonium lignum sulphate, 50% by weight solution
*parts by volume

EXAMPLE 4

Field Trials

In this experiment the drift of propanil aerially applied to a test field in Sacramento County, Calif., U.S.A. was monitored. To assure the reliability of the trials, care was taken to select a rice field isolated from adjacent local fields which had been recently sprayed or which were to be sprayed with propanil in the near future.

In the experiment Propanil 4E concentrate of Cedar Chemicals was used. 40 acres of a 300 acre rice field were aerially sprayed with propanil formulation containing per acre:

| Propanil 4E concentrate | 5.0 qt. |
|---|---|
| Ammonium lignin sulfonate (ORZAN A) | 4.0 lb. |
| epoxidized canola oil | 5.0 qt. |
| water | 11.5 gal. |

The air from the field was sampled continuously for 3 days following the application from two in-field locations (A and B) through 8"×10" filters at an air flow of 70 ft$^3$ min$^{-1}$. Filters were changed at 12 hour intervals with the exception of a filter from the actual application (changed after 4 hours) and the final filter (changed after 24 hours). The amounts of propanil collected on the filters were determined by gas chromatography. The results of the analysis are shown in Table 6.

The data show that the air above the trial field did not contain propanil for 72 hours at wind speeds up to 30 mph. Both the 6-B filter and a windward control filter No. 2, in line with the filter 6-B, showed contamination at wind speeds up to 20 mph, which suggests a contamination by propanil drifting from a greater distance.

As propanil crystals can be traced to more than 5 miles from the application site, an "adjacent plot" control would not be entirely reliable and none was used. Instead of an "adjacent plot" control, contamination values established in similar tests by the Agricultural Engineering Department of the University of California at Davis were used for comparison. These control data had been collected with 4 inch diameter filters operated 3.5 hours daily at an air flow rate of 16 ft$^3$ min$^{-1}$ and were recalculated for comparison with the sampling conditions of the experiment. The recalculated values fell within a range of 0.045 mg to 0.249 mg of propanil per filter, with an average of 0.149 mg. Compared with these data the results of the experiment show a substantial reduction in the quantity of propanil transported off the area of application.

TABLE 6

| Sample Number | Propanil, milligrams |
|---|---|
| 1-A* | <0.1 (undetectable) |
| 1-B* | ≧0.1 |
| 2-A | <0.1 |
| 2-B | <0.1 |
| 3-A | <0.1 |
| 3-B | <0.1 |
| 4-A | <0.1 |
| 4-B | <0.1 |
| 5-A | <0.1 |
| 5-B | <0.1 |
| 6-A | <0.1 |
| 6-B** | ≧0.1 |
| Control #1*** | <0.1 |
| Control #2**** | ≧0.1 |

*The filter was operated during the actual aerial application.
External contamination (see below, **).
***A control filter operated prior to the aerial application.
****This filter was from a windward location to the trial indicating the propanil was in the airstream before it flowed over the trial field; and this contamination was consistent with the filter Number 6-B.

EXAMPLE 5

Field trials

A trial similar to that described in Example 4 was installed near Griffith, New South Wales, Australia. In this trial another propanil concentrate ("Ronacil" of Schering) was used. A field was aerially sprayed at a rate of 10 gallons/acre with a propanil formulation containing an epoxidized soy oil and having the following composition:

| propanil concentrate | 1.6 gallons |
|---|---|
| ammonium lignin sulfonate (50% by weight aqueous solutions) | 1 gallon |
| epoxidized soy oil | 1 gallon |
| water | 6.4 gallons |

The air sampling procedure was similar to that described in Example 4 but carried out from one in-field location. The results of the analysis of the filters are shown in Table 7. It is to be noted that despite the higher content of propanil in the spraying formulation the contamination of filters was in each case (except for the filter operated during the application) below the detectable level and significantly less than the control value of 0.149 mg (see Example 4).

TABLE 7

| Sample Number | Propanil, mg |
|---|---|
| NSW #1 | >0.3* (300 g) |

TABLE 7-continued

| Sample Number | Propanil, mg |
|---|---|
| NSW #2 | <0.1 (undetectable) |
| NSW #3 | <0.1 |
| NSW #4 | <0.1 |
| NSW #5 | <0.1 |
| Blank Filter | <0.1 |

*Filter was operated during the aerial application

EXAMPLE 6

Efficacy test-epoxidized canola/soy oil replicated trial

A four material-four replicate plot design (4×4) trial was installed at Yanko Agricultural Experimental Institute, New South Wales, Australia. The plots were 2 meters wide by 10 meters in length. Plot design included randomization. "Ronacil" of Schering was used as propanil concentrate. The applications of spraying formulations were made with a carbon dioxide pressured sprayer using Spraying Systems (Wheaton, Ill.) #80015 nozzles at 20" centers. The application rate was 10 gallons/acre, at mph and 40 psi, at a temperature of 33° C and winds of from 3 to 5.8 mph. Samples of watergrass plants were collected three days after application. Table 8 summarizes the design and the results of the experiment. The results show the phytotoxicity of propanil and propanil/epoxidized canola oil formulations. Whereas the untreated plants were not inhibited in their growth (average stem weight of 3.8 grams per plant), the treated plant had their growth inhibited (average stem weight from 1.128 to 2.2045 grams per plant, depending on formulation).

TABLE 8

Application detail (amounts of components in parts by volume):

| Plot No. | Propanil | Soy oil | Canola | AL-50 | Water |
|---|---|---|---|---|---|
| 1 | 1 | 1 | 0 | 1 | 7 |
| 2 | 1 | 0 | 1 | 1 | 7 |
| 3 | 1 | 1 | 0 | 0 | 8 |
| 4 | 1 | 0 | 0 | 0 | 9 |
| 5 | 0 (Control) | 0 | 0 | 0 | 0 |

Results:

| Watergrass | Stem Count | Total weight grams | Average stem grams |
|---|---|---|---|
| No. 1 | 50 | 56.40 | 1.1280 |
| No. 1 | 32 | 63.96 | 1.9987 |
| No. 2 | 50 | 64.32 | 1.2864 |
| No. 3 | 42 | 92.59 | 2.2045 |
| No. 4 | 40 | 83.22 | 1.6644 |
| Control | 75 | 285.21 | 3.8028 |

EXAMPLE 7

Efficacy test—epoxidized soy oil field trial

This trial was installed near Griffith, new South Wales, Australia. "Ronacil" of Schering was used as propanil concentrate.

A 4.5 ha plot integral in a 60 ha rice field was aerially sprayed at a rate of 16 liters per hectare with a formulation having the following composition:

| propanil concentrate | 1 gallon |
|---|---|
| ammonium lignin sulfonate (50% by weight aqueous solution) | 1 gallon |
| epoxidized soy oil | 1 gallon |
| water | 7 gallons |

3 days after application samples of barnyard grass were collected and measured. Table 9 summarizes the results which show the inhibition of the growth of treated plants and the effectiveness of the treatment in terms of both the average wet weight per stem and the average dry weight per stem for untreated and treated plants.

TABLE 9

| | Count | Total Weight grams | Av wt/stem grams |
|---|---|---|---|
| First sampling (wet weights) | | | |
| Treatment | 75 stems | 185.71 | 2.4761 |
| Control | 60 stems | 260.46 | 4.3410 |
| Second Sampling (dry weights) | | | |
| Treatment | 50 stems | 80.80 | 1.616 |
| Control | 50 stems | 259.91 | 5.182 |

What I claim as my invention is:

1. A method for reducing and controlling pesticide drift caused by crystallization of a pesticide from a pesticide spraying formulation, which method comprises incorporating an epoxidized vegetable oil into the formulation.

2. A method according to claim 1, wherein the spraying formulation comprises water as a diluent.

3. A method according to claim 1, wherein the vegetable oil is canola oil or soy oil.

4. A method according to claim 1, wherein the ratio of the pesticide in the form of 50% by weight liquid concentrate to the epoxidized vegetable oil is from about 1:10 to about 10:1 by volume.

5. A method according to claim 4, wherein the ratio is about 1:1.

6. A method according to claim 1, wherein the spraying formulation additionally includes lignin sulfonate.

7. A method according to claim 6, wherein the lignin sulfonate is ammonium lignin sulfonate.

8. A method according to claim 7, wherein the ratio of the pesticide in the form of 50% by weight liquid concentrate to ammonium lignin sulfonate in the form of 50% by weight agueous solution is from about 1:10 to about 10:1 by volume.

9. A method according to claim 8, wherein the ratio is about 1:1.

10. A method according to claim 1, wherein the pesticide is a herbicide.

11. A method according to claim 10, wherein the herbicide is propanil.

12. A method according to claim 1, wherein the pesticide is propanil and the vegetable oil is canola oil.

13. A pesticide spraying formulation comprising a pesticide, a diluent and an epoxidized vegetable oil.

14. A formulation according to claim 13, wherein the diluent is water.

15. A formulation according to claim 13, wherein the pesticide is a herbicide.

16. A formulation according to claim 13, wherein the vegetable oil is canola oil or soy oil.

17. A formulation according to claim 13, wherein the ratio of the pesticide in the form of 50% by Weight liquid concentrate to the epoxidized vegetable oil is from about 1:10 to about 10:1 by volume.

18. A formulation according to claim 17, wherein the ratio is about 1:1.

19. A formulation accordinq to claim 13 additionally including lignin sulfonate.

20. A formulation according to claim 19, wherein the lignin sulfonate is ammonium lignin sulfonate.

21. A formulation according to claim 20, wherein the ratio of the pesticide in the form of 50% by Weight liquid concentrate to ammonium lignin sulfonate in the form of 50% by weight aqueous solution is from about 1:10 to about 10:1 by volume.

22. A formulation according to claim 21, wherein the ratio is about 1:1.

23. A formulation according to claim 13, wherein the pesticide is propanil, the diluent is water and the vegetable oil is canola oil.

24. A formulation according to claim 17, wherein the pesticide is propanil, the diluent is water and the vegetable oil is canola oil.

25. A formulation according to claim 21, wherein the pesticide is propanil, the diluent is water and the vegetable oil is canola oil.

* * * * *